(12) United States Patent
Nielsen

(10) Patent No.: US 7,331,965 B2
(45) Date of Patent: Feb. 19, 2008

(54) MEASURING EQUIPMENT FOR USE IN CONNECTION WITH HIP PROSTHESIS SURGERY

(76) Inventor: Poul Torben Nielsen, Bangsbovej 8, DK-9200 Alborg SV (DK)

( * ) Notice: Subject to any disclaimer, the term of this patent is extended or adjusted under 35 U.S.C. 154(b) by 290 days.

(21) Appl. No.: 10/532,102

(22) PCT Filed: Oct. 21, 2003

(86) PCT No.: PCT/DK03/00714

§ 371 (c)(1),
(2), (4) Date: Apr. 21, 2005

(87) PCT Pub. No.: WO2004/034904

PCT Pub. Date: Apr. 29, 2004

(65) Prior Publication Data

US 2006/0015121 A1    Jan. 19, 2006

(30) Foreign Application Priority Data

Oct. 21, 2002   (DK) ............................... 2002 01601

(51) Int. Cl.
*A61B 17/58* (2006.01)

(52) U.S. Cl. .................................................... 606/102
(58) Field of Classification Search ................ 606/81, 606/91, 102; 600/201–248, 587; 33/512
See application file for complete search history.

(56) References Cited

U.S. PATENT DOCUMENTS

| 4,987,904 A * | 1/1991 | Wilson ........................ 600/587 |
| 5,141,512 A | 8/1992 | Farmer et al. |
| 5,213,112 A | 5/1993 | Niwa et al. |

FOREIGN PATENT DOCUMENTS

| EP | 0860143 | 8/1998 |
| FR | 2684287 | 6/1993 |

* cited by examiner

*Primary Examiner*—Eduardo C. Robert
*Assistant Examiner*—Nicholas Woodall
(74) *Attorney, Agent, or Firm*—James Creighton Wray; Clifford D. Hyra

(57) ABSTRACT

The invention concerns a measuring instrument, preferably for use in connection with press fit hip prosthesis surgery, whereby it is possible to measure/register size (diameter) and modulus of elasticity of acetabulum and femur for inserting an uncemented socket or uncemented femur component.

14 Claims, 8 Drawing Sheets

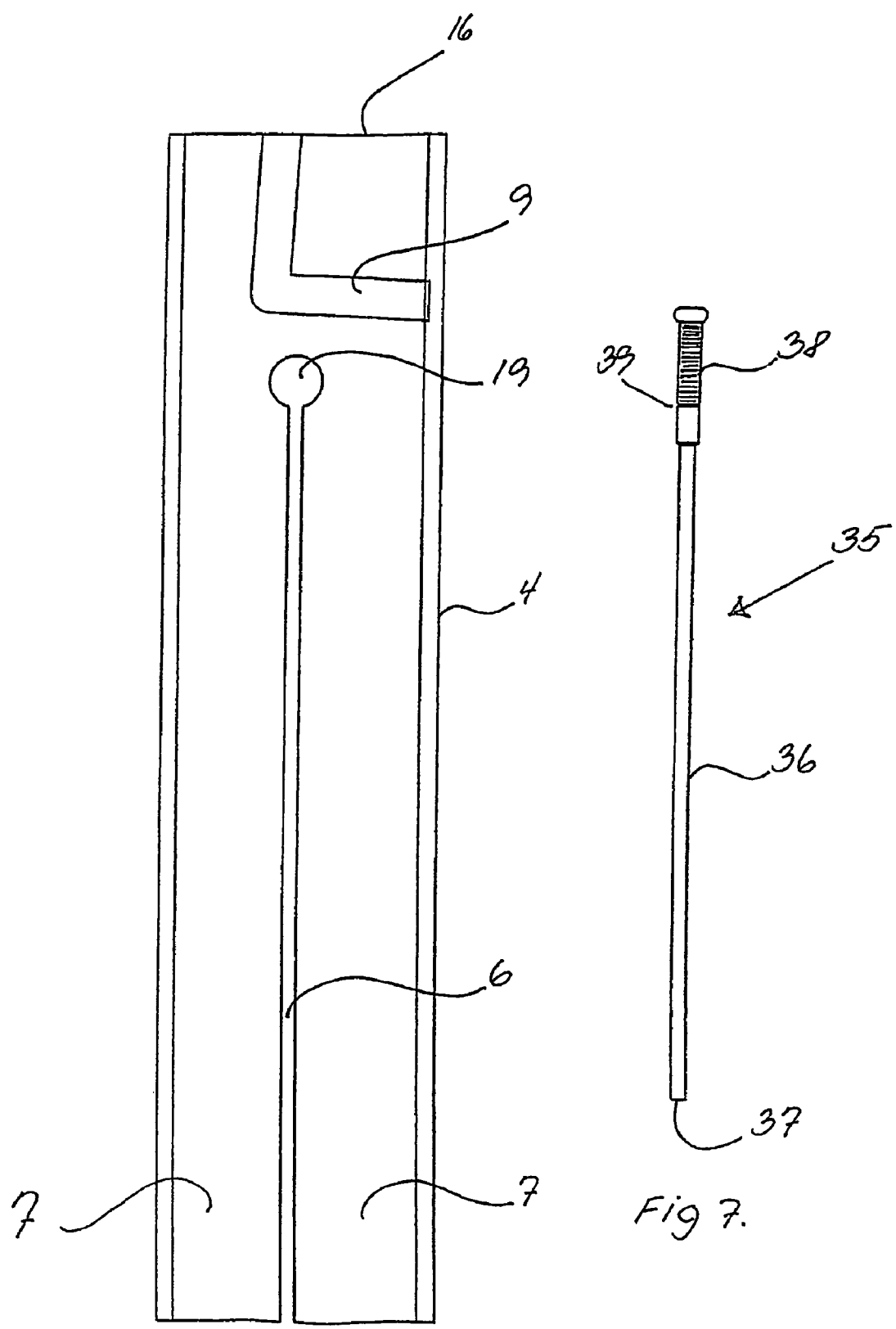

MEASURING EQUIPMENT FOR USE IN CONNECTION WITH HIP PROSTHESIS SURGERY

This application claims the benefit of Danish Application No. PA 2002 01601 filed Oct. 21, 2002 and PCT/DK2003/000714 filed Oct. 21, 2003, which are hereby incorporated by reference in their entirety.

SCOPE OF THE INVENTION

The present invention concerns a measuring instrument, preferably for use in connection with hip prosthesis surgery.

BACKGROUND OF THE INVENTION

Through the last 35-40 years bone cement has been used for anchoring prosthesis components when inserting artificial hip joints. Good results have been achieved with this technique, but after long time observation of large groups of patients, problems have been detected with loosening of the inserted prosthesis component. Furthermore, a considerable bone loss has occurred around the prosthesis component so that a replacement surgery is made difficult.

Through the years, alternative techniques in the shape of uncemented sockets, where the socket is anchored in acetabulum, have been developed. Different anchoring methods have been developed, and the method appearing to provide good results on short as well as long view is the use of metal sockets, preferably made of materials as e.g. titanium or vitalium. These metal sockets are typically hemispherical with a porous surface.

The surface of the metal socket is applied a so-called porous coating implying that the surface is rough and provides possibility of ingrowth of bone cells into the surface of the metal socket. The surface coating of a metal socket typically has a pore size of 50-250 μm and may either consist of small metal balls or metal fibres that are compressed or sprayed on. A supplementing hydroxapatite coating promotes the bone ingrowth process.

When inserting an uncemented porously coated metal socket, a hole fitting the metal socket to be inserted is milled in acetabulum. E.g. if acetabulum is milled up to 60 mm, a 60 mm metal socket is inserted. Then the metal socket is anchored further with 2-4 screws through holes in the metal socket. However, screw anchoring has appeared to have unfavourable effects, as the polyethylene decomposition product can migrate through the screw holes and out into the bone, and here produce osteolysis or necrosis of the bone.

In order to avoid the latter, in later years another anchoring method has been used, consisting in that a so-called "press-fit" technique has been used, where e.g. acetabulum is milled up to 60 mm in diameter, where subsequently is inserted e.g. a 62 mm or 64 mm metal socket. A great tension is thereby achieved between bone and metal socket, whereby the metal socket is held in place without supplementing use of screws. In the course of the first weeks after the operation, the bone then grows from the pelvis into surface coating of the metal socket and ensures the so-called secondary anchoring.

The described technique is, however, rather demanding and requires an experienced physician to perform the hip prosthesis surgery, as there is risk of problems if the metal socket has not been correctly inserted. If the metal socket is not securely clamped, there is risk that it may loosen in the course of the first days after the operation. If the metal socket is too strongly clamped, there is great risk of fracture in the pelvis bone around the metal socket whereby it becomes unstable.

Therefore, it is important to insert the right size of metal socket. In order to determine which size of metal socket to be used, previously a template or a test prosthesis has been used and placed in acetabulum and which by a light pressure is fixed in acetabulum, after which is selected a metal socket in the same size or with 1-2 mm oversize.

However, it is not a good and objective method of measuring, and one may risk to use/insert more than one metal socket in order to let it fit optimally. A great disadvantage by this method is that a metal socket that has been in contact with a patient cannot be autoclaved and used for another patient. This metal socket is to be discarded, which also implies increased costs in connection with a hip prosthesis surgery.

In patent publications FR 2 684 287 and U.S. Pat. No. 5,141,512 there is described equipment for measuring in connection with placing of a hip socket, but not decidedly measuring the size and the elasticity of acetabulum.

Until now, no equipment has been developed with which the physician can measure the hip socket and thereby objectivise this part of the procedure of hip surgery. E.g. the risk of fracture in the hip socket depends on the elasticity in the bone and the size of the acetabulum. Furthermore, it also has great significance whether it is a first time operation or a replacement operation.

OBJECT OF THE INVENTION

It is the purpose of the present invention to indicate a measuring instrument which in a simple way can measure/register the size and the elasticity as well as the shape of acetabulum. This implies that hip prosthesis operations become safer, and the costs of these operations are reduced.

This is achieved according to the present invention with a measuring instrument of the kind mentioned in the introduction, which is peculiar in that the measuring instrument includes:

an adapter including a measuring head and a connector, where the measuring head is provided with a largely hemispherical surface in which there is a central through-going bore, where the measuring head is divided into at least two separate sections, where the connector is hollow and slotted at one end in axial direction of the measuring head into a number of legs, the number of legs corresponding to the number of the at least two separate sections of the measuring head, where the legs of the connector are each connected to one of the at least two sections of the measuring head on the rear side of the hemisphere, where a securing arrangement is provided at the opposite end of the connector relative to the connection to the measuring head;

a measuring unit including a actuating rod, where a main part having preferably conical shape that can interact displaceably axially with the central bore of the adapter and thereby change the diameter of the measuring head of the adapter, a mounting ring where means for engaging the securing arrangement of the adapter are provided, where the mounting ring is connected with a handle member, where in connection with the handle member there is provided means for axial displacement of the actuation rod and registration of the relative displacement of the actuation rod relative to the measuring head;

a depth gauge including a first part, which is preferably a smooth rod, and a second part with stop and measurement indications, where the depth gauge is provided for interacting with a through-going opening in the axial direction of the measuring instrument.

DESCRIPTION OF THE INVENTION

A measuring instrument according to the invention will make it easy and simple to measure the diameter of an acetabulum by a hip operation.

Before inserting a metal socket in acetabulum, the measuring instrument is used in that:
  an adapter with a measuring head with a desired diameter is coupled to the measuring unit by means of the coupling arrangement and the mounting ring,
  the measuring head of the adapter is inserted into the acetabulum so that the lower edge of the hemispherical measuring head fits with the circumferential rim of the acetabulum,
  by actuating the handle means for axial displacing the actuation rod, the actuation rod will perform an axial displacement towards the measuring head,
  by the axial displacement, the main part of the actuation rod will interact with the preferably conical opening inside the measuring head and thereby force the separate sections of the measuring head outwards,
  spreading of the separate sections of the measuring head cause the diameter of the hemispherical measuring head to expand, whereby the measuring head is clamped in the acetabulum,
  at a certain pre-tensioning, the diameter of the measuring head is read,
  the depth gauge is used for measuring the possible distance from the surface of the measuring head and down into the bottom of the acetabulum,
  after measuring diameter and depth of the acetabulum, the handle means are actuated for axial displacement of the actuation rod so that the actuation rod performs an axial displacement in against the handle, and the measuring head may be removed from the acetabulum.

In order to place the measuring head of the adapter in the acetabulum and being sure that the right diameter of the acetabulum is measured, the spherical surface of the adapter measuring head is provided with at least two different surfaces, a rough surface on the lower part of the spherical surface, and a smooth surface on top of the spherical surface.

The rough surface provides for better engagement of the spherical surface of the grooved/milled bone tissue of the acetabulum. By using the measuring instrument, the measuring head is placed against the edge of the acetabulum, whereby the rough surface prevents displacing of the measuring head during expansion of the measuring head. The rough surface may be provided with different patterns which can be an arbitrary number of strings, linear and/or crossing flutes and/or beads.

Since only a few acetabuli have largely hemispherical shape, it is not necessary that the entire spherical surface of the measuring head has a rough surface. Therefore a part of the spherical surface of the measuring head is provided with a smooth surface, since a smooth surface will be easier to keep clean and thereby more hygienic.

In a preferred embodiment of the invention, the adapter is connected with the measuring unit in that the securing arrangement of the adapter are recesses for a bayonet socket, and that the mounting ring of the measuring unit, where means for engaging the securing arrangement of the adapter are provided, are designed as pins for a bayonet engagement.

By using a bayonet engagement it is possible to readily assemble the adapter with the measuring unit. Furthermore, a bayonet engagement is not a difficult assembly to manufacture, irrespectively whether the adapter is cast in one or the connector of the adapter is a pipe.

Alternative embodiments for the securing arrangement between the adapter and the measuring unit may e.g. be:
  a screw thread providing a very stable assembly, but having the drawback that it may be difficult to clean;
  a snap lock performing a releasable engagement when the adapter is placed in the measuring unit, implying easy and quick replacement of an adapter, but having the drawback that they may be worn out and thereby cannot hold the adapter in the measuring unit.

If the measuring instrument is made of a sufficiently cheap material, the adapter and the measuring unit may be made in one piece. This implies that for each hip operation, a series of measuring instruments with different diameter of the measuring head are to be used. Following use, the used measuring instruments are to be discarded or autoclaved.

For the measuring head of the adapter to expand while at the same time the adapter being easy and cheap to manufacture, the adapter is to be designed so that the adapter is made of a hard yet flexible material which e.g. may be one or more of the following: a metal alloy, a plastic material, e.g. a plastic composite, and/or ceramic material.

It will be an advantage to avoid joints in the adapter and, if the adapter is made of a metal alloy, that the adapter is made in one piece where the adapter either is cast with cutouts and recesses, or that they are made subsequently. Furthermore, the metal is also to have a certain temperature resistance as an adapter made in a metal alloy will be an expensive equipment and is therefore to be autoclaved after use.

In a preferred embodiment of the invention, the adapter is made of a hard yet flexible plastic composite, e.g. PDM or the like. By making the adapter of a plastic composite, the adapter may either be moulded in the same way as when making an adapter of a metal alloy, or it may be rotationally moulded, where the subsequent processing of making of slots and recesses may readily be performed afterwards.

In an alternative embodiment of the invention, the adapter may be made in a ceramic material where a health effect may be achieved, since metals or plastics are not to be introduced in an open operation region. When using ceramics, a suitable manufacturing method is to be found so that the measuring head of the adapter may expand. A suitable manufacturing method may, however, increase the cost of making adapters.

However, it is important that all materials are heat resistant, so that irrespectively of the material the adapter and the measuring unit are made of, it is to be possible to autoclave the entire measuring instrument or parts of the measuring instrument.

In order that the measuring head of the adapter may expand by an axial movement, the preferably conical main part of actuation rod will interact with a face and/or edge of the central through-going bore inside the measuring head of the adapter.

In neutral position of the actuation rod the at least two separate sections of the measuring head are largely gathered, and by axial displacing of the actuation rod, the at least two separate sections of the measuring head will be pressed away from each other, and the diameter of the measuring head will expand with Up to 4 mm. A greater expansion of the diameter of the measuring head than 4 mm may cause fracture in acetabulum.

The central through-going bore in the axial direction enables passing the actuation rod through the connector, up inside and out through the measuring head. The bore in the measuring head is designed so that it is preferably conical.

The main part of the actuation rod, the shape of which is conical, will by axial displacement of the main part of the actuation rod into the preferably conical bore in the measuring head cause the three sections of the main part to be pressed away from each other.

In an alternative embodiment of the through-going bore in the measuring head and/or the main part of the actuation rod, it is e.g. possible that:

the through-going bore in the measuring head is designed as a straight bore and the main part of the actuation rod is designed largely conical, or ball-shaped, whereby the main part of the actuation rod interacts with a rim part of the through-going bore in the measuring head;

the through-going bore in the measuring head is designed largely conical, or with curved faces, and the main part of the actuation rod is designed as a rod with increased diameter in relation to the actuation rod itself, whereby the upper edge section of the main part of the actuation rod interacts with surfaces of the through-going bore in the measuring head;

the through-going bore in the measuring head is designed largely conically or with curved faces, and the main part of the actuation rod is designed largely conical or spherical, whereby surfaces of the main part of the actuation rod interacts with surfaces of the through-going bore in the measuring head.

In the two first alternatives, it will be necessary to safeguard the faces of either the through-going bore in the measuring head or the main part of the actuation rod, as they are to interact with an edge section of the opposing part. By repeated actuation of the actuation rod, wear may occur where the edge section hits the opposing surface. A safety measure may be surface coating of the exposed surfaces, or by making the measuring head and the main part of the actuation rod of materials with different hardness, so that the item with the edge part is made of the softest material.

The adapter is designed with a measuring head which is largely hemispherical and divided into at least three sections. This division is made in order to achieve a satisfactory contact of the surface of the spherical face against the acetabulum, particularly by expansion of the measuring head.

These sections are connected to the legs of the connector which are provided by one end of the connector being slotted in axial direction. The slotting provides that the connector can absorb the forces coming from the ball head when it expands.

In a preferred embodiment of the invention, means of axial displacement of the actuation rod is a millimetre screw device. Such a millimetre screw device will enable placing the measuring head of the adapter in an acetabulum, make it fit and thus, without further actuation in axial direction, enable screwing on the millimetre screw device so that the actuation rod is displaced axially into the measuring head bore, and thereby increasing the diameter of the measuring head.

Such a millimetre screw device includes a spring in connection with an adjustment part and a swivel ring with one or more measuring indicators. Furthermore, it may also be a ratchet function inside the millimetre screw device.

In an embodiment of the invention, the millimetre screw device is made so that it may "click over" (overload protection) in order to avoid too much expansioning of the measuring head, and too strong clamping of the measuring head in the acetabulum, which may lead to fracture of the acetabulum.

The measuring indicators on the measuring ring and on the measuring unit provide that by counting turns of the swivel ring and by reading measuring units by means of conversion factor, the increase of the diameter of the measuring head may be determined.

The adjusting part is used every time a new adapter is inserted in the measuring instrument, whereby the measuring instrument is adjusted to neutral position.

In an alternative embodiment of the invention, the means for axial displacement of the actuation rod has been selected among one or more of the following: hydraulics, pneumatics and/or electricity driving a motor or a unit that interact with the actuation rod.

In order to enable fine adjustment of the diameter of the measuring head in the acetabulum, it may be an advantage that axial displacement of the actuation rod is motorised. Besides that it will not be the the doctor's ability of setting the measuring instrument which is decisive for the socket size, at the same time problems with holding the measuring head in the socket simultaneously with screwing or moving the actuation rod manually in axial displacement are avoided. This will make the measuring instrument lighter and the measurements more objective in use.

For measuring the actual displacement of the actuation rod, registration of the relative displacement of the actuation rod in relation to the measuring head occurs by reading one or more measuring indications applied on the handle.

These measuring indicators are to be applied clearly so that a user of the measuring instrument does not confuse the measurements read, which may cause a wrong metal socket to be pressed into the acetabulum, whereby problems like bad fixation of the metal socket or fracture in acetabulum may arise.

In an embodiment of the invention, the measuring instrument is connected to a computer for controlling and/or registering the relative displacement of the actuation rod relative to the measuring head.

In a further embodiment of the invention, the measuring instrument may be used for collecting data on a computer connected thereto. This computer may either be coupled to the motor/unit and thereby measure the turns that correspond to a certain relative displacement, or be coupled to a measuring arrangement which is capable of measuring, e.g. by means of optics, lasers or the like, how long the relative displacement of the actuation rod is in relation to a fixed point in the measuring instrument.

By collecting data so that one may have a large database in the computer, whereby more and more experience is collected as to how an acetabulum is shaped concurrently with more and more data being registered with the measuring instrument. This makes it easier and quicker to find the socket fitting optimally with acetabulum.

Furthermore, such a system with a computer for controlling and registering will be a good tool in teaching inexperienced/new physicians for hip/prosthesis operations as experiences from previous operations are stored in the database. This makes it possible for the doctors performing hip prosthesis surgery to draw on experiences/information before they commence the operation.

In order to optimise the hip prosthesis operation, it is important for the doctors to measure the pressure to which the acetabulum is subjected at the insertion of the metal socket, as the pressure most likely will be different with regard to different groups of patients. E.g. it may be difficult to achieve sufficient stability of the metal socket in patients with osteopsathyrosis.

The pressure exerted by the metal socket on acetabulum may be measured simultaneously with measuring the diameter of acetabulum with a measuring instrument according to this invention. The measuring instrument is provided with a pressure registering unit connected to the measuring head, so that simultaneously with registration of the increase of the diameter the pressure action of the measuring head on acetabulum is measured.

The pressure registration unit may e.g. be pressure transducers that are provided in or on the measuring head. They are, however, to be durable and securely fastened as the measuring head is forced around in acetabulum in order to ensure selection of the correct metal socket.

Alternatively, piezo-electric crystals may be used for pressure registration on the measuring head.

By comparing pressure measurement, diameter of the metal socket and the patient's data, the doctors may reduce the problems with loose metal sockets and fracture of acetabulum implying that the patient is immediately to undergo a new operation or is to have a replacement operation earlier than expected.

In order to have a flexible system for measuring acetabulum during hip operation, the adapter for use in the measuring instrument is replaceably connected with the measuring unit of the measuring instrument. This provides for the adapter and the measuring unit being made of different materials.

An adapter will typically be made of a more cheap material than the measuring unit, whereby it is possible to practice a method where an adapter is used once and then discarded. This results in saving of autoclaving of an adapter after use, as well as the risk of infection or other unwanted contamination is reduced.

Furthermore, by using a replaceable adapter it is possible to provide a series of adapters with different diameter of the measuring head, where the measuring head diameter in neutral position may vary from 45 to 85 mm, preferably between 50 and 70 mm.

It is advantageous to provide an adapter series where the measuring head has different diameter, as the measuring instrument may be used for all types of hip operations by replacing the adapter. This means that a measuring instrument with adapter with a small measuring head may be used for persons by pelvis operations where the acetabulum does not have so large diameter, whereas an adapter with large diameter is preferably used in pelvis operations where the acetabulum has large diameter.

A series of adapters with different diameters of the measuring head is provided with diameters in steps of about 2 mm measured when the measuring head of the adapter is in neutral position and is not influenced by the actuation rod. However, the step size of the measuring head diameter of the adapter is to be maximum 3 mm if the diameter of the adapter measuring head can expand up to 4 mm.

This implies that the adapter is not to be brought to an extreme position of its measuring range before it is required/possible to exchange the adapter with an adapter with greater measuring head diameter. Thereby, for an inexperienced and/or unskilled physician there is achieved a rapid and more precise measurement of the diameter of the acetabulum.

Furthermore, it implies that it is easier to find an adapter that largely fits into the acetabulum, after which the actual diameter of the acetabulum is produced by fine adjustment of the measuring unit.

For adapters made of a material by which it is economically advantageous to reuse the adapters after autoclaving, it is a further advantage that by repeated use of an adapter there is not exerted an unnecessary stress on the legs on the connector of the adapter due to large expansions of the measuring head. The adapter may hereby be used more times and last longer.

An adapter that fits within about 2 mm when inserted in an acetabulum will facilitate the work in measuring the diameter of the acetabulum as the doctor is not simultaneously to hold the measuring head of the adapter in position in the acetabulum so that the rough surface of the measuring head engages the edge of the acetabulum and to screw/turn or displace the actuation rod.

When the diameter of the metal socket to be inserted in the acetabulum has been found, the measuring instrument is designed so that a depth gauge interacts with a through-going opening in the axial direction of the measuring instrument.

In the preferred embodiment, the depth gauge will be provided through a central through-going opening in the axial direction of the measuring instrument so that it goes through the measuring unit, out through the actuation rod and out through the through-going bore of the adapter. This implies that the depth gauge by mounting through the measuring unit will project at the point of the ball-shaped measuring head of the adapter.

The depth gauge is used for measuring the depth of acetabulum so that it may be determined how much bone implant (artificial bone mass and/or bone mass taken from the patient) which is to be disposed between acetabulum and metal socket in order that the metal socket is provided a natural and solid bed in acetabulum.

On the depth gauge is indicated a measuring indication so that in neutral position a first measuring mark is indicated, after which measuring markings with suitable spacing are indicated. This spacing between the measuring indications will typically indicate one or two millimetre at a time.

The principles described in the present invention may also find application in connection with insertion of uncemented prosthesis components in other human joints, e.g. in the marrow cavity of the femur or in the neck of the femur.

BRIEF DESCRIPTION OF THE DRAWINGS

The invention will then be explained more closely with reference to the accompanying drawing, where:

FIG. 6 shows the connector of the adapter, FIG. 7 shows the depth gauge of the measuring instrument.

DETAILED DESCRIPTION OF THE INVENTION

Figure 1:
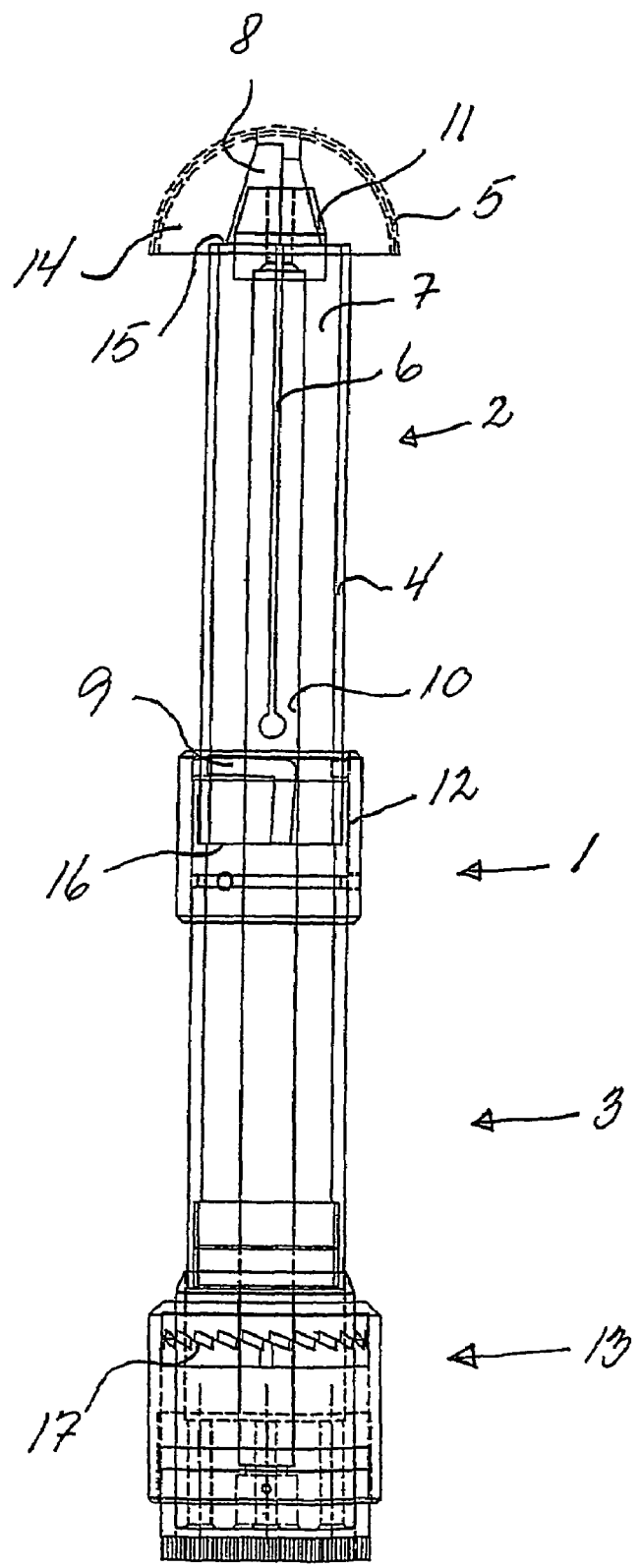
FIG. 1 shows a measuring instrument according to the invention.

In FIG. 1 is shown a measuring instrument 1 including an adapter 2 and a measuring unit 3.

The adapter 2 includes a connector 4 and a measuring head 14 that has a hemispherical surface 5. The connector 4 has at least two axially extending slots 6 dividing the end 15 of the connector 4 into a number of legs 7. The measuring head 14 includes a hemispherical surface S divided into a number of sections (not shown) so that each part is connected with one leg 7 of the connector 4. At the end 16 of the connector 4 are provided recesses 9 that are designed to interact with corresponding pins (not shown) provided in the mounting ring 12 of the measuring unit 2. Inside the measuring unit 14 is provided an axially through-going conical bore 8 which is designed to interact with the actuation rod 10 of the measuring unit 3.

The measuring unit 3 includes an actuation rod 10, a mounting ring 12 and a millimetre screw device 13. The actuation rod 10 has a conical main part 11 which by axial displacement and engagement with the conical bore 8 in the measuring head 14 forces the separate sections (not shown) of the measuring head 14 from each other. The outward going force caused by the displacement of the actuation rod 10 in relation to the conical opening 8 of the measuring head is absorbed in bending the legs 7 of the connector 4.

The mounting ring 12 is provided with pins (not shown) which is designed to engage the recesses 9 in the end 16 of the adapter 2.

In order to achieve axial displacement of the actuation rod 10 in relation to the conical opening 8 of the measuring head 14, the measuring unit 3 is provided as a millimetre screw device 13 which by rotation axially displaces the actuation rod 10. Inside the millimetre screw device 13 is provided a releasable ratchet device 17 that ensures tightening of the millimetre screw device 13.

Figure 2:
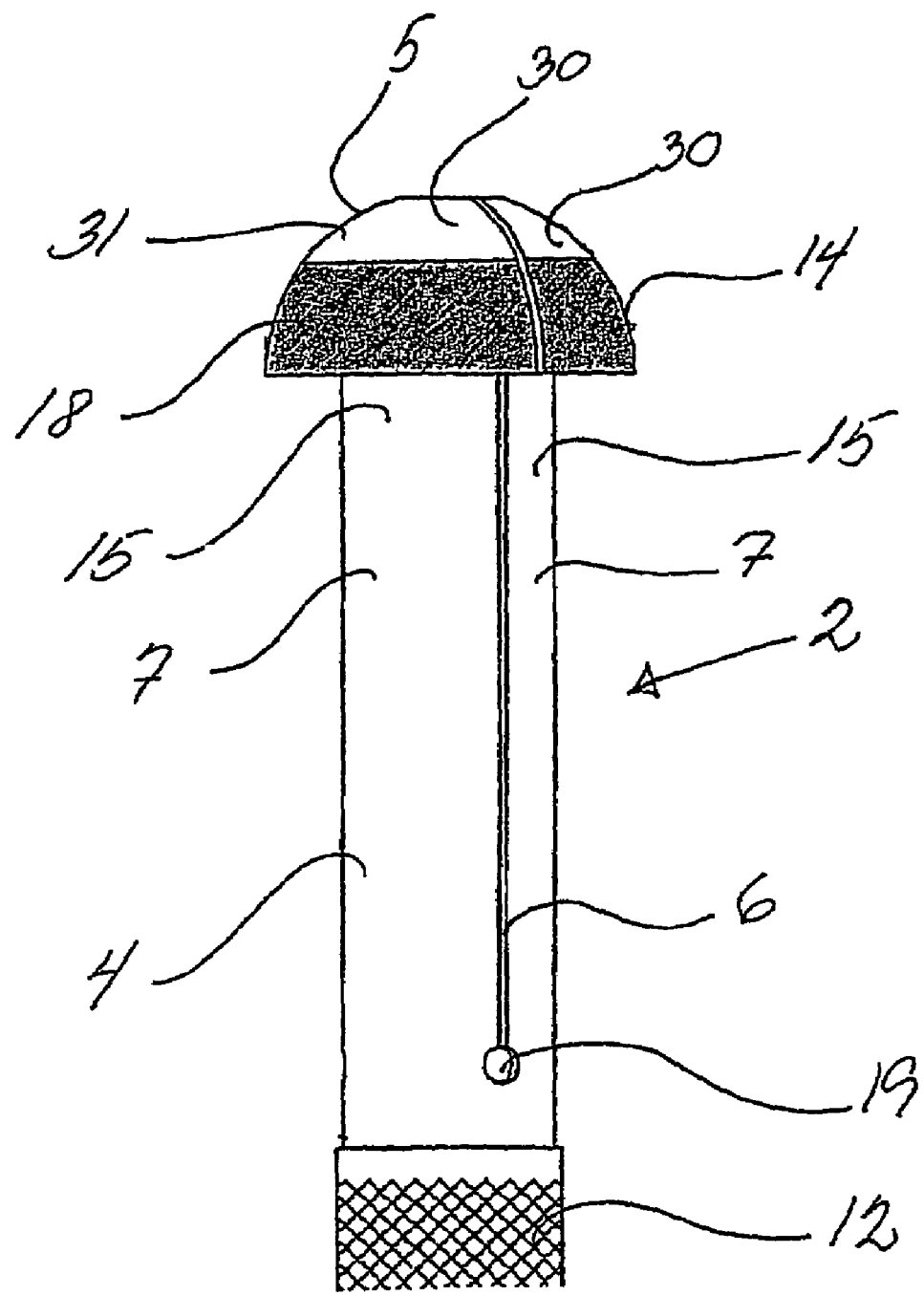
FIG. 2 shows a side view of an adapter according to the invention.

FIG. 2 shows the adapter 2 which includes a connector 4 and a measuring head 14 having a hemispherical surface 5. In the connector 4 there is shown axially extending slots 6 that divide the end 15 of the connector 4 into a number of legs 7. The slot 6 ends in a circular opening 19 that prevents notch effect in the connector 4 when the measuring head 14 expands.

The measuring head 14 includes a hemispherical surface 5 which is divided into a number of sections 30 each connected with one of the legs 7 of the connector 4. The hemispherical surface 5 of the measuring head 14 is divided into two areas with different roughness: a top part 31 with smooth surface and a bottom part 18 with rough surface.

Figure 3:
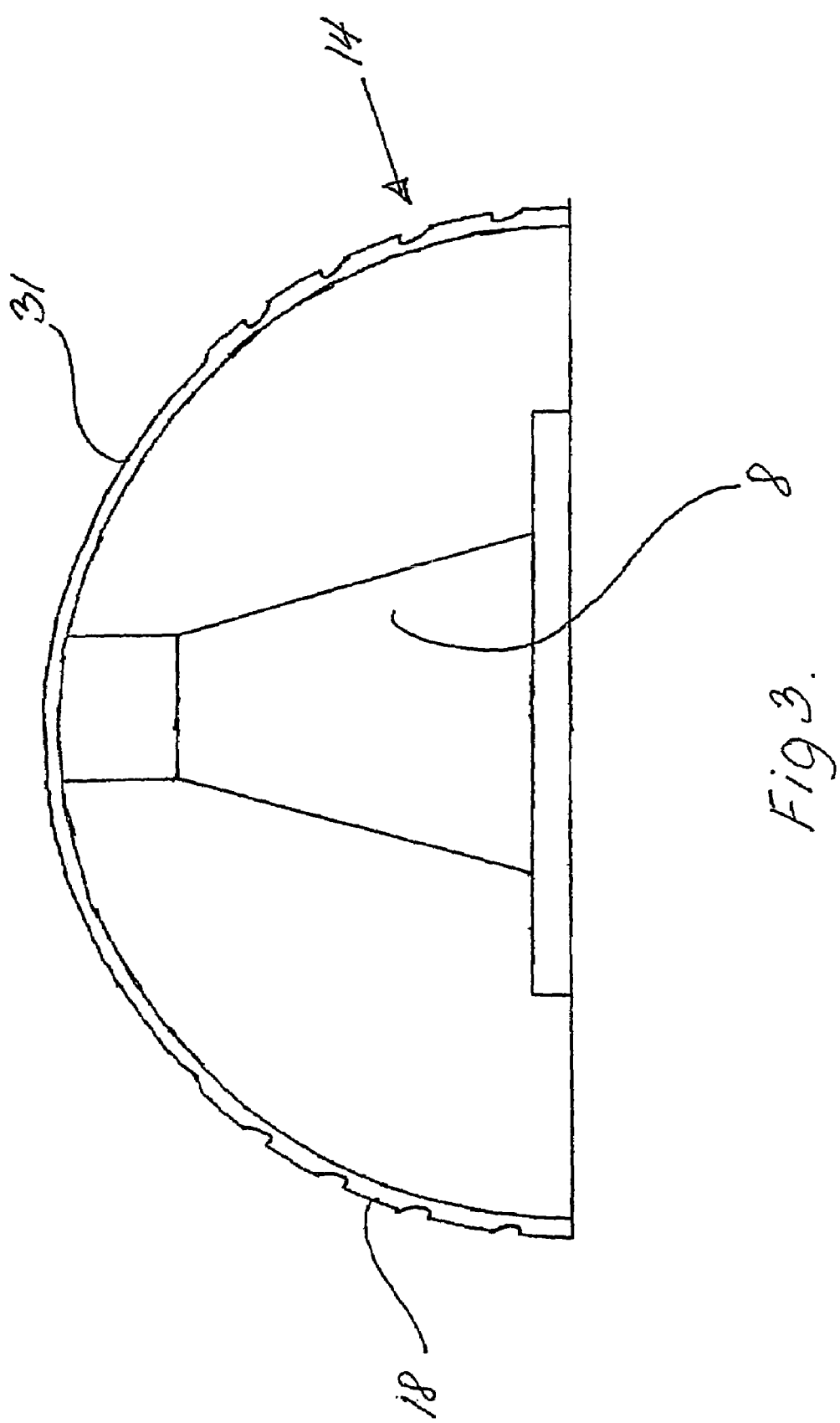
FIG. 3 shows a cross-section of the measuring head of the adapter.

FIG. 3 shows a cross-section in the measuring head 14. Inside the measuring head 14 is provided an axial through-going conical bore 8 which is designed to interact with actuation rod (not shown). In order to bear against and produce some resistance against acetabulum, the surface 5 of the measuring head 14 is divided into a top part 31 with a smooth surface and a bottom part 18 with a rough surface.

Figure 4:
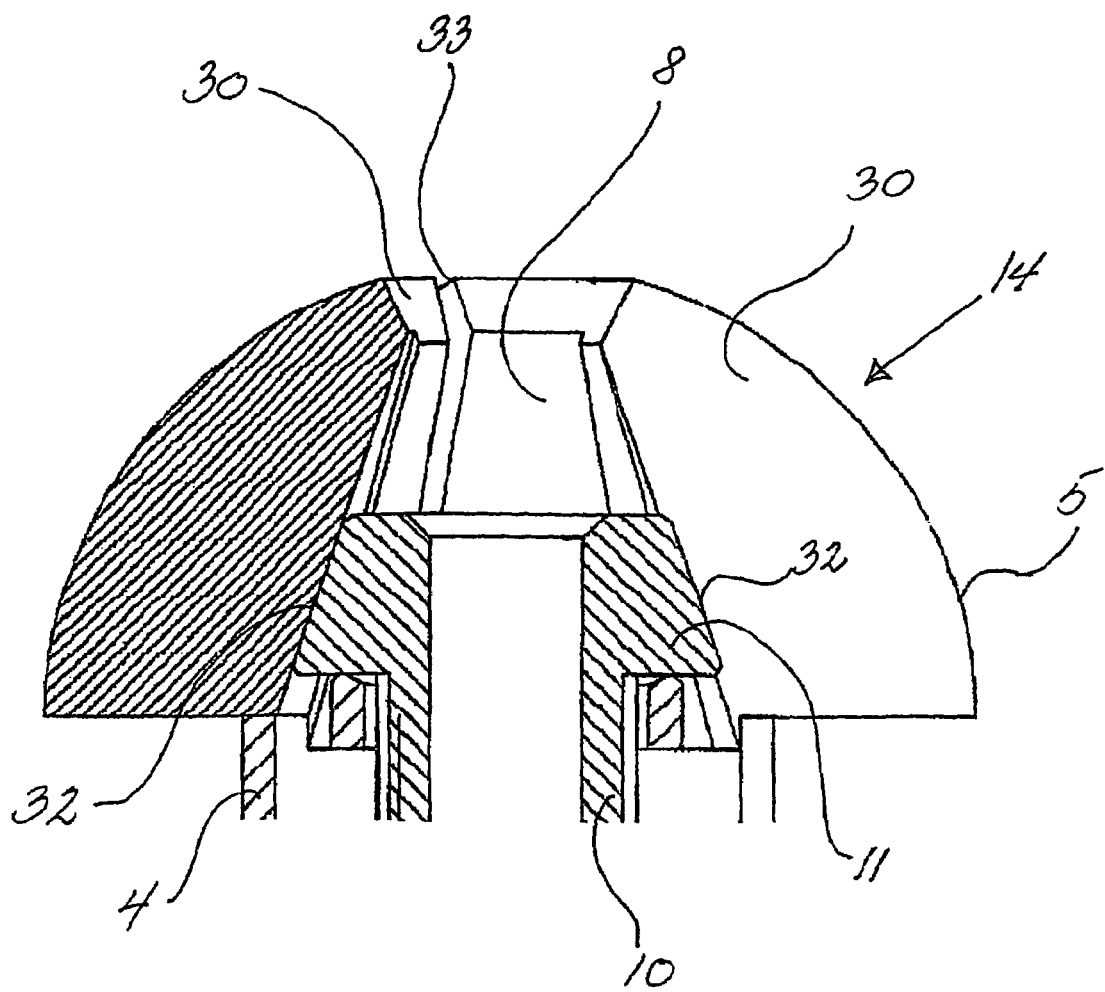
FIG. 4 shows a cross-section of the interaction between measuring head and an actuation rod.

FIG. 4 shows a cross-section of the measuring head 14 by actuation of the actuation rod 10, where the conical main part 11 of the actuation rod 10 is engaging the conical opening 8 of the measuring head 14. An upwards directed axial displacement of the actuation rod 10 will result in the sides 32 on the conical main part 11 of the actuation rod 10 forcing the sections 30 of the measuring head from each other, and the slot 33 will be enlarged.

Figure 5:
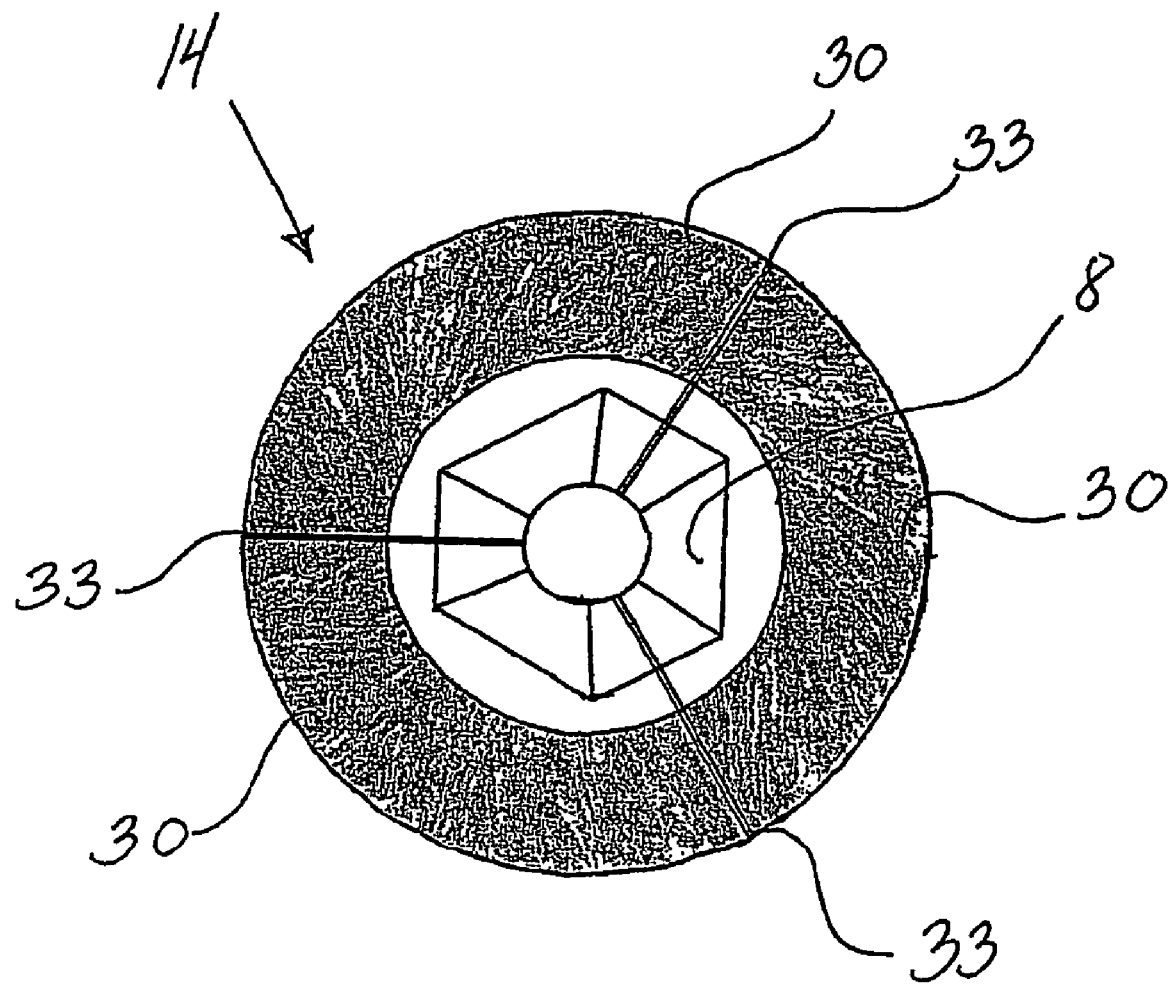
FIG. 5 shows a plan view of the measuring head.

FIG. 5 shows a plan view of a measuring head 14 as seen from the bottom and up through the conical opening 8. The three sections 30 of the measuring head are separated by the slots 33.

FIG. 6 shows the connector 4 of the adapter 2 in which is provided a slot 6 opening into a circular opening 19 that divides the connector 4 in the legs 7. Furthermore is shown a recess 9 at the end 16 of the connector 4 which is designed to interact with corresponding pins (not shown) provided in the (not shown) mounting ring of the measuring unit.

FIG. 7 shows the depth gauge 35 of the measuring instrument 1 that together with the measuring instrument 1, where a through-going opening corresponding with the diameter 35 of the depth gauge has been provided inside through all the components of the measuring instrument 1. The depth gauge preferably includes a long, slender body part 36 terminating in an end part 37, which by use of the depth gauge 35 during use of the measuring instrument (not shown) reaches the bottom of the reamed acetabulum (not shown). At the opposite end, there is a handle part 38 enabling the doctor to operate the depth gauge 35. At the side of the handle 38 there are provided a number of measuring indications 39 indicating the depth (volume) of the cavity between a metal socket (not shown) of a given diameter and acetabulum.

Figure 8:
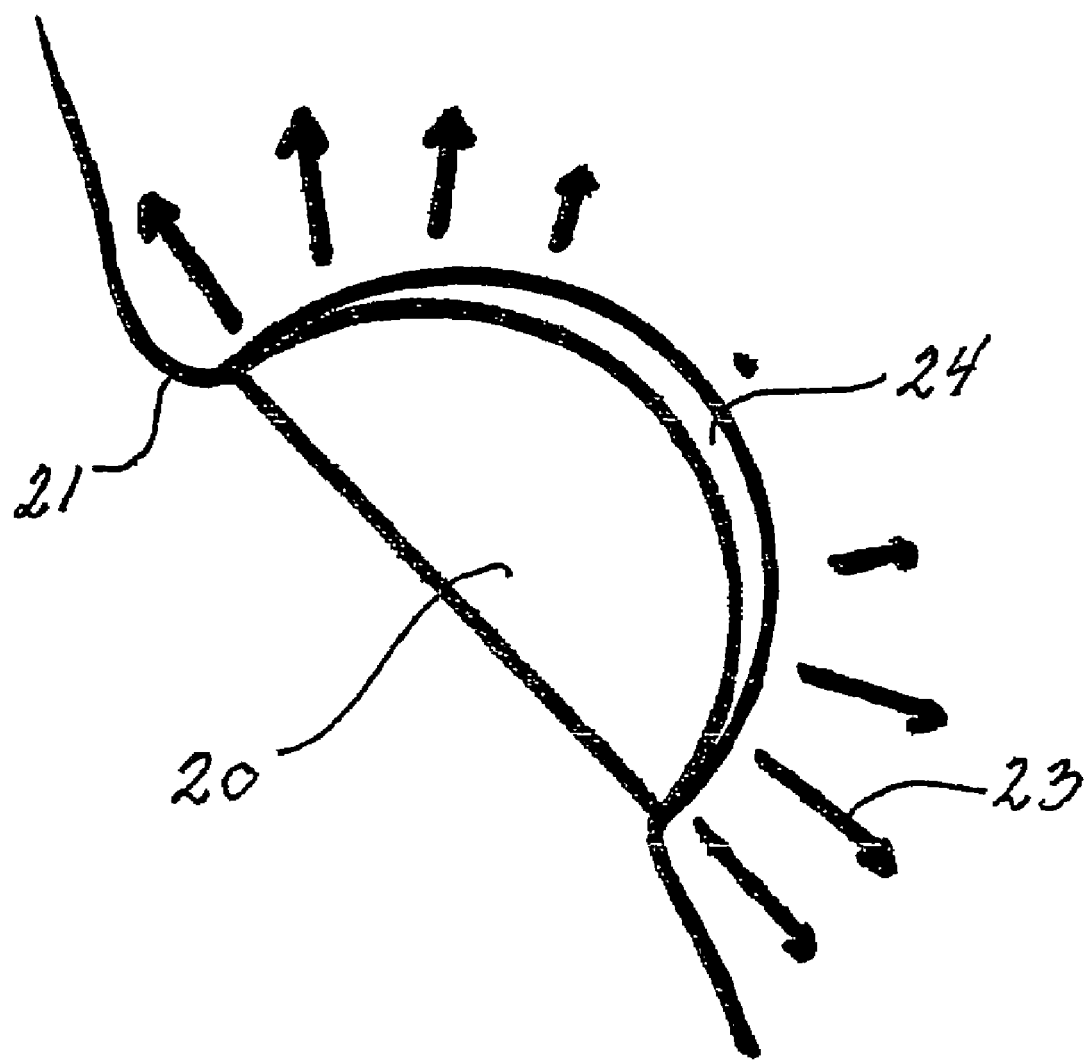
FIG. 8 shows a cross-section of a metal socket inserted in acetabulum.

FIG. 8 shows a metal socket 20 inserted in an acetabulum 21. The metal socket 20 is inserted according to the press-fit technique and is oversize compared with acetabulum 21. Therefore, the outwards directed forces 23 will arise, and the metal socket 20 will be securely anchored in the acetabulum. Behind the metal socket 20 an interspace 24 typically appears which is filled with bone mass so that the metal socket 20 is secured in a natural and solid bed in acetabulum 21. It is the depth of this interspace 24 which is measured with the depth gauge (not shown).

Figure 9:
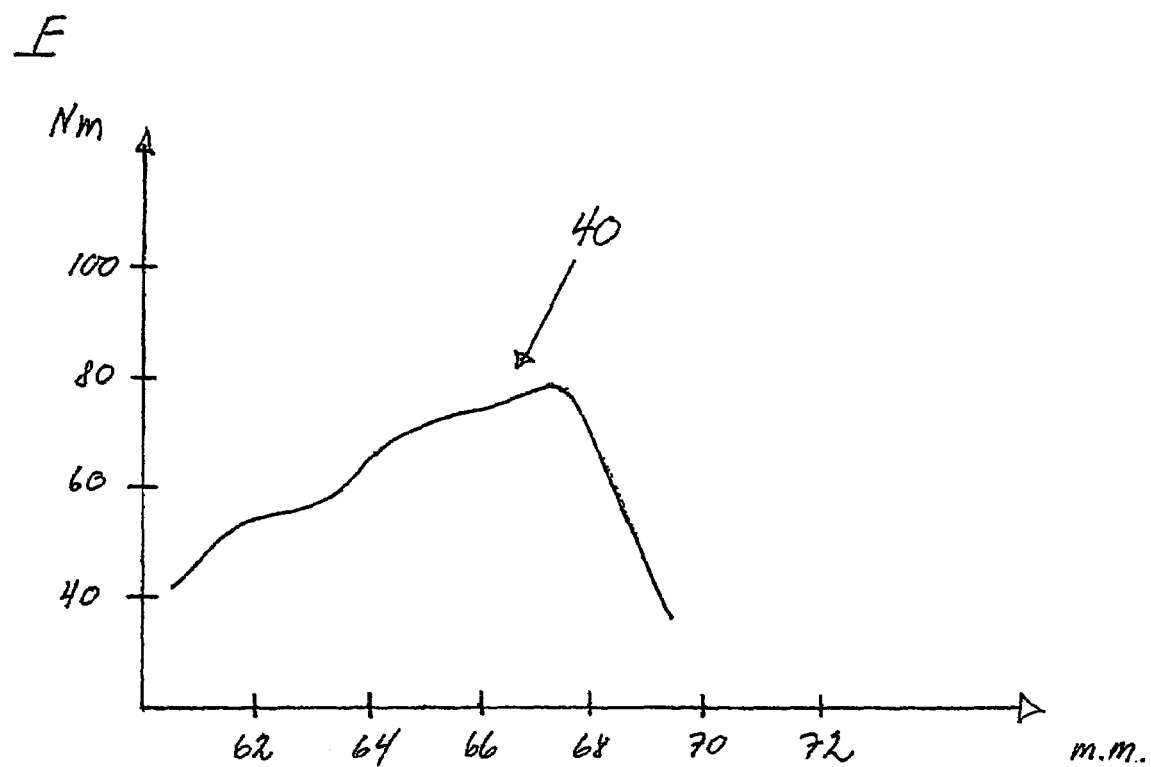
FIG. 9 shows a graph of the relation between the force with which the measuring head acts on acetabulum and the diameter of the measuring head.

It is the outwards directed forces 23 that are very necessary in the long nm for measuring in order to optimise hip prosthesis operations. FIG. 9 shows a graph over the outwards directed forces 23 and the diameter of the measuring head 14. The graph 40 shows the correlation between the force F [Nm] with which the metal sockets acts on acetabulum, particularly the sides in the inlet hole.

The example illustrated in FIG. 9 is for a patient having reamed a 64 mm hole in acetabulum. By inserting a measuring head of 64 and subsequently expanding the measuring head, the force F will be increased until the measuring head has expanded so much that it causes fracture. The fracture is illustrated by the graph 40 dropping drastically when the diameter goes up to 68 mm or more.

As such a fracture is not only dependent on the size of the inserted measuring head/metal socket, but also on the bone condition of the patient, it will be a great advantage if the force F is measured while using the measuring instrument.

The invention is not limited to the embodiments shown in the Figures and described above. Other embodiments including other kinds of coupling arrangements between adapter and measuring head, surface and internal shapes of the measuring head of the adapter and methods of driving the actuation rod are conceivable within the frames of this invention and the features specified in the claims.

The invention claimed is:

1. Measuring instrument, preferably for use in connection with hip prosthesis surgery, characterised in that the measuring instrument includes:

an adapter including a measuring head and a connector, where the measuring head is provided with a largely hemispherical surface in which there is a central through-going bore, where the measuring head is divided into at least two separate sections, where the connector is hollow and slotted at one end in axial direction of the measuring head into a number of legs, the number of legs corresponding to the number of the at least two separate sections of the measuring head, where the legs of the connector are each connected to one of the at least two sections of the measuring head on the rear side of the hemisphere, where a securing arrangement is provided at the opposite end of the connector relative to the connection to the measuring head;

a measuring unit including a actuating rod, where a main part has a conical shape that can interact displaceably axially with the central bore of the adapter and thereby change the diameter of the measuring head of the adapter, a mounting ring where means for engaging the securing arrangement of the adapter are provided, where the mounting ring is connected with a handle member, where in connection with the handle member there is provided means for axial displacement of the actuation rod and registration of the relative displacement of the actuation rod relative to the measuring head;

a depth gauge including a first part, which is preferably a smooth rod, and a second part with stop and measurement indications, where the depth gauge is provided for interacting with a through-going opening in the axial direction of the measuring instrument.

2. Measuring instrument according to claim 1, characterised in that spherical surface of the measuring head of the adapter is provided with at least two different surfaces, a rough surface at the lower part of the spherical surface and a smooth surface on top of the spherical surface.

3. Measuring instrument according to claim 1, characterised in that the securing arrangement of the adapter are recesses for a bayonet socket.

4. Measuring instrument according to claim 1, characterised in that adapter is made of a hard yet flexible material, such as a metal alloy, a plastic material, e.g. a plastic composite, and/or ceramic material.

5. Measuring instrument according to claim 1, characterised in that the preferably conical main part of the actuation rod interacts with a face and/or edge of the central through-going bore inside the measuring head of the adapter, where in neutral position of the actuation rod the at least two separate sections of the measuring head are largely gathered, and by axial displacing of the actuation rod, the at least two separate sections of the measuring head will be pressed away from each other, and the diameter of the measuring head will expand with up to 4 mm.

6. Measuring instrument according to claim 1, characterised in that mounting ring of the measuring unit, where means for engaging the securing arrangement of the adapter have been provided, is designed as pins for a bayonet socket.

7. Measuring instrument according to claim 1, characterised in that means for axial displacement of the actuation rod is a millimetre screw device.

8. Measuring instrument according to claim 7, characterised in that the millimetre screw device includes a spring in connection with an adjusting member and a swivel ring with one or more measuring indications.

9. Measuring instrument according to claim 1, characterised in that means for axial displacement of the actuation rod is one or more of the following: hydraulics, pneumatics and/or electricity driving a motor or unit interacting with the actuation rod.

10. Measuring instrument according to claim 1, characterised in that registration of the relative displacement of the actuation rod relative to the measuring head is effected by reading one or more measuring indications on the measuring handle.

11. Measuring instrument according to claim 1, characterised in that the measuring instrument is connected to a computer for controlling andlor registering the relative displacement of the actuation rod in relation to the measuring head of the relative displacement of the actuation rod.

12. Measuring instrument according to claim 1, characterised in that the adapter is exchangeably connected with the measuring unit of the measuring instrument.

13. Measuring instrument according to claim 1, wherein in that the adapter is provided in a series with different diameters of the measuring head, where the diameter of the measuring head in a neutral position can vary from 45 to 85 mm.

14. Measuring instrument according to claim 13, wherein the diameter of the measuring head in a neutral position can preferably vary between 50 mm and 70 mm.

* * * * *